(12) United States Patent
Kwon (10) Patent No.: US 11,051,710 B2
(45) Date of Patent: Jul. 6, 2021

(54) BIOELECTRICAL IMPEDANCE ANALYSIS SYSTEM AND METHOD FOR DETERMINING A BODY IMPEDANCE

(71) Applicant: ams AG, Premstaetten (AT)

(72) Inventor: Jun Kwon, Yongin-si (KR)

(73) Assignee: AMS AG, Premstaetten (AT)

( * ) Notice: Subject to any disclaimer, the term of this patent is extended or adjusted under 35 U.S.C. 154(b) by 436 days.

(21) Appl. No.: 16/078,930

(22) PCT Filed: Mar. 20, 2017

(86) PCT No.: PCT/EP2017/056554
§ 371 (c)(1),
(2) Date: Aug. 22, 2018

(87) PCT Pub. No.: WO2017/162585
PCT Pub. Date: Sep. 28, 2017

(65) Prior Publication Data
US 2019/0053736 A1    Feb. 21, 2019

(30) Foreign Application Priority Data
Mar. 23, 2016  (EP) ..................................... 16162020

(51) Int. Cl.
*A61B 5/0537* (2021.01)
*A61B 5/00* (2006.01)

(52) U.S. Cl.
CPC .......... *A61B 5/0537* (2013.01); *A61B 5/6815* (2013.01); *A61B 5/6823* (2013.01);
(Continued)

(58) Field of Classification Search
None
See application file for complete search history.

(56) References Cited

U.S. PATENT DOCUMENTS

2003/0216665 A1   11/2003   Yoshihisa
2014/0051940 A1   2/2014    Messerschmidt

FOREIGN PATENT DOCUMENTS

EP   1 118 308   7/2001
EP   1 138 259   10/2001
(Continued)

OTHER PUBLICATIONS

ISA/EP, International Search Report for PCT/EP2017/056554 (dated May 18, 2017).
(Continued)

*Primary Examiner* — Eric F Winakur
*Assistant Examiner* — Marjan Fardanesh
(74) *Attorney, Agent, or Firm* — MH2 Technology Law Group LLP (57) ABSTRACT

A body impedance analysis, BIA, system comprising a host and an accessory device connectable to the host device via a data cable. A first and a second electrode are arranged on an outside of the accessory device and a third and a fourth electrode are arranged on an outside of the host device. A BIA circuitry is connected to the third and the fourth electrode and connectable to the first and the second electrode via the data cable. The BIA circuitry is configured to drive an alternating current through the body via the first and the third electrode, to sense a voltage indicative of a body impedance via the second and the fourth electrode and to determine the body impedance depending on the sensed voltage.

13 Claims, 3 Drawing Sheets

(52) U.S. Cl.
CPC .......... *A61B 5/6824* (2013.01); *A61B 5/6897* (2013.01); *A61B 5/6829* (2013.01); *A61B 2560/0468* (2013.01)

(56) References Cited

FOREIGN PATENT DOCUMENTS

| | | |
|---|---|---|
| WO | 2014/035223 | 3/2014 |
| WO | 2015/102156 | 7/2015 |

OTHER PUBLICATIONS

Bedogni, G., et al., "Accuracy of an eight-point tactile-electrode impedance method in the assessment of total body water," European Journal of Clinical Nutrition, 56:1143-1148 (Jan. 1, 2002) (http://www.nature.com/ejcn/journal/v56/n11/pdf/1601466a.pdf).

# BIOELECTRICAL IMPEDANCE ANALYSIS SYSTEM AND METHOD FOR DETERMINING A BODY IMPEDANCE

BACKGROUND OF THE INVENTION

The disclosure relates to a bioelectrical impedance analysis, BIA, system and a method for determining a body impedance, in particular by means of a BIA system. More specifically, the disclosure relates to a BIA system implemented in a portable electronic host device with an accessory device.

Bioelectrical impedance analysis, also denoted as body impedance analysis, may for example be used to determine biological parameters of a body, for example a human body, in particular a body fat percentage or another biological parameter related to an impedance of the body.

For BIA, two-terminal measurement methods may be applied. A disadvantage of such methods may be a reduced measurement accuracy due to a contact resistivity between electrodes of a BIA system and the skin of the user of the BIA system.

Approaches to implement a BIA system based on four-terminal measurement in a portable electronic device may suffer from the fact that only a limited distance between individual electrodes of the BIA system, in particular of the four-terminal measurement arrangement, may be realized due to the given size of the portable electronic device. This may lead to a decreased measurement accuracy, in particular of the determination of the body impedance.

SUMMARY OF THE INVENTION

The present disclosure provides an improved concept for performing BIA by means of a portable electronic device with an improved measurement accuracy.

In the following, the expression "connected" includes at least "directly connected" and "switchably connected".

According to the improved concept, two electrodes of a four-terminal sensing arrangement of a BIA system are implemented on an outside of a portable electronic host device, while two further electrodes of the sensing arrangement are implemented on an outside of an accessory device connectable to the host device via a data cable. A current is driven through a body of a user of the BIA system via one electrode of the host device and one electrode of the accessory device and a resulting voltage indicative of the body impedance is measured by means of the two remaining electrodes. A BIA circuitry comprised by the host device is configured to determine the body impedance depending on the sensed voltage.

According to the improved concept, a BIA system comprising a portable electronic host device and an accessory device connectable to the host device via a data cable is provided. The BIA system further comprises a first and a second electrode arranged on an outside of the accessory device for contacting a first and a second contact area of a body of the user, respectively. The BIA system further comprises a third and a fourth electrode arranged on an outside of the host device for contacting a third and a fourth contact area of the body, respectively. The BIA system, in particular the host device, further comprises a BIA circuitry being connectable to the first and the second electrode via a first and a second line of the data cable, respectively.

The BIA circuitry is connected to the third and the fourth electrode and is configured to drive an alternating current through the body via the first and the third electrode. The BIA circuitry is further configured to sense a voltage indicative of a body impedance of the body via the second and the fourth electrode and to determine the body impedance depending on the sensed voltage.

According to some implementations, the host device is implemented as or comprises a mobile phone, a smartphone, a tablet computer, a notebook computer or a portable media player, for example a portable music player.

According to some implementations, the accessory device is implemented as or comprises an earphone device.

The earphone device may comprise ear speakers, earphones, earbuds, headphones, circumaural headphones, circumaural earphones, supra-aural headphones or supra-aural earphones.

The first and the second electrode are arranged on the outside of the accessory device, for example the earphone device, for example such that the user may establish a contact between the first and the second electrode and the first and the second contact area of his body, for example by applying the first and the second electrode to the first and the second contact area, respectively, and/or by touching the third and the fourth electrode.

In some implementations, in particular in implementations where the accessory device is implemented as an earphone device, the first and the second electrode are arranged on respective positions of the earphone device to contact the first and the second contact area when the user wears the earphone device.

In this way, a contact between the first and the second electrode and the first and the second contact area, respectively, may for example be established without any specific action by the user being necessary.

The third and the fourth electrode are arranged on the outside of the host such that the user may establish a contact between the third and the fourth electrode and the third and the fourth contact area of his body, for example by applying the third and the fourth electrode to the first and the second contact area, respectively, and/or by touching the third and the fourth electrode.

According to some implementations, the third and the fourth electrode are comprised by a component of the host device such as a housing, a case, a frame, a cover or a back-cover. In particular, the third and the fourth electrode may be implemented as respective metal parts of said components of the host device and may be electrically isolated from each other.

According to some implementations, the third and the fourth electrode are arranged on the outside of the host device such that a contact between the third and the fourth electrode and the third and the fourth contact area, respectively, is established when the user holds the host device in his hand.

Consequently, a seamless determination of the body impedance may be achieved by means of the improved concept. In particular, the current may be driven, the voltage may be sensed and the body impedance may be determined by means of the BIA system during regular usage of the host device and the accessory device by the user.

The contact areas of the body may in particular be respective areas on the skin of the body.

The described arrangement of the four electrodes corresponds to a four-terminal arrangement for sensing the body impedance. Therein, the first and the third electrode correspond, for example, to force connections or current leads of the four-terminal arrangement, while the second and the fourth electrode correspond, for example, to sense connections or voltage leads of the four-terminal arrangement.

According to some implementations, the BIA circuitry is configured to sense the voltage indicative of the body impedance by measuring an amplitude value of a voltage dropping across the second and the fourth electrode and a phase shift, in particular a phase shift between a phase of the alternating current driven through the body and the sensed voltage, in particular the voltage dropping across the second and the fourth electrode.

It is highlighted that, according to the improved concept, the body impedance and the biological parameter are for example neither determined nor evaluated by the accessory device depending on the sensed voltage, but exclusively by means of the host device. The accessory device for example solely provides the first and the second electrode.

This arrangement may have the particular advantage that no processing unit, such as a microcontroller unit, necessarily has to be provided in the accessory device.

Since the first and the second electrode are arranged on the accessory device, while the third and the fourth electrode are arranged on the host device, a spatial separation of the first and the third electrode as well as a spatial separation of the second and the fourth electrode may be increased. In particular a length of an electrically conducting path between the first and the third electrode as well as between the second and the fourth electrode may be increased. This may lead to an improved accuracy of the four-terminal sensing and consequently to an improved accuracy of the determined body impedance.

According to some implementations, the accessory device is implemented as or comprises a wristband, an ankle-band, a belt or a chest belt.

According to some implementations of the BIA system, the BIA circuitry comprises an interface unit configured to drive the alternating current through the body and to sense the voltage indicative of the body impedance.

According to some implementations, the interface unit is further configured to determine an amplitude value of the sensed voltage and a phase shift of the sensed voltage with respect to the alternating current. The interface unit may, for example, be implemented as a dedicated biometrical circuit, in particular a biometrical integrated circuit.

According to some implementations of the BIA system, the interface unit is configured to determine the body impedance depending on the amplitude value and the phase shift.

According to some implementations of the BIA system, the BIA circuitry comprises a processing unit of the host device configured to determine the body impedance depending on the amplitude value and the phase shift.

According to some implementations, the processing unit corresponds to or is comprised by an application processor of the host device, in particular if the host device is implemented as a smartphone, a tablet computer or a portable media player.

According to some implementations of the BIA system, the BIA circuitry, in particular the processing unit, is configured to determine at least one biological parameter of the body depending on the body impedance.

According to some implementations of the BIA system, the BIA circuit is configured to determine the at one least biological parameter by means of one or more lookup tables relating the determined body impedance to the at least one biological parameter. The at least one lookup table is, for example, stored in a storage unit of the host device.

According to some implementations of the BIA system, the at least one biological parameter comprises at least one of the following: a body fat percentage, BFP, a fat mass, FM, a total body water value, TBW, a fat-free mass value, FFM, a lean body mass value, LBM, a body cell mass, BCM, an extracellular mass, ECM.

According to some implementations of the BIA system, the BIA circuitry, in particular the interface unit, comprises a voltage sensing unit for sensing the voltage indicative of the body impedance.

According to some implementations of the BIA system, the voltage sensing unit comprises a first terminal connected to the fourth electrode and a second terminal connectable to the accessory device via the second line.

According to some implementations of the BIA system, the BIA circuitry, in particular the interface unit, comprises a current source for driving the current through the body.

According to some implementations of the BIA system, the current source comprises a first terminal connected to the third terminal and a second terminal connectable to the accessory device via the first line.

According to some implementations of the BIA system, the first electrode is connected to a ground terminal of the accessory device and the second terminal of the current source is connected to a ground terminal of the host device. When the accessory device is connected to the host device via the data cable, the first line connects the ground terminals of the accessory device and the host device to each other.

According to some implementations of the BIA system, the first line is useable as a ground line when the accessory device is connected to the host device via the data cable.

Consequently, the first line may advantageously be used as a ground line and as a line for supplying the alternating current from the host device to the accessory device simultaneously.

According to some implementations of the BIA system, the second electrode is connected to the second line via a switch of the accessory device when the accessory device is connected to the host device via the data cable. The second terminal of the voltage sensing unit is connected to the second line via a switch of the host device when the accessory device is connected to the host device via the data cable.

In such implementations, the second line of the data cable may advantageously be used for sensing the voltage indicative of the body impedance selectively with another usage of the second line. For example, the second line may be used as a microphone line or speaker line when the switches of the accessory device and the host device do not connect the second terminal of the voltage sensing unit and the second electrode to each other.

According to some implementations of the BIA system, the first electrode is connected to the first line via a further switch of the accessory device when the accessory device is connected to the host device via the data cable. The second terminal of the current source is connected to the first line via a further switch of the host device when the accessory device is connected to the host device via the data cable.

According to some implementations of the BIA system, the accessory device comprises a control unit, for example for receiving a control input from the user, and the first and the second electrode are arranged on an outside of the control unit.

The control unit may, in particular if the accessory device is implemented as an earphone device, be implemented as a volume control unit of the accessory device and/or as a control unit for accepting, ending and/or rejecting a telephone call, in particular if the host device is implemented as a mobile phone or a smartphone.

In such implementations, the user may touch the first and the second electrode if the user intends that the BIA system should determine the body impedance and/or the at least one biological parameter.

According to some implementations of the BIA system, the data cable is implemented as an audio cable.

According to some implementations of the BIA system, the data cable is comprised by the BIA system, in particular by the accessory device.

According to some implementations of the BIA system, the data cable comprises an audio jack, for example a three-, a four-, or a five-pole audio jack.

According to some implementations of the BIA system, the data cable comprises a USB connector, for example a USB-C connector.

The host device is, for example, connectable to the accessory device via an audio socket of the host device and the audio jack or via a USB socket of the host device and the USB connector.

According to some implementations of the BIA system, the second line is usable as a microphone line, in particular to transmit microphone data between the host device and the accessory device, or as a speaker line, in particular for transmitting speaker signals between the host device and the accessory device, when the accessory device is connected to the host device via the data cable.

The second line may, for example, be usable as microphone line or speaker line, in particular when the voltage sensing unit and the second electrode are disconnected from the second line, in particular by the switches of the host device and the accessory device, respectively.

Such implementations may be particularly advantageous since it is not necessary to include an additional line for the first and/or the second line to supply the alternating current from the host device to the accessory device or for sensing the voltage. Rather, the existing microphone line, speaker line and/or ground line of the data cable may be reused for these purposes.

In implementations where the second line is usable as speaker line, the second line may simultaneously or selectively be used as the speaker line and for sensing the voltage indicative of the body impedance.

According to the improved concept, also a method for determining a body impedance using a BIA system is provided. The BIA system comprises a portable host device and an accessory device connected to the host device via a data cable. The method comprises contacting a first contact area of a body of a user of the BIA system with a first electrode arranged on an outside of the accessory device and contacting a second contact area of the body with a second electrode arranged on an outside of the accessory device. The method further comprises contacting a third contact area of the body with a third electrode arranged on an outside of the host device and contacting a fourth contact area of the body with a fourth electrode arranged on the outside of the host device.

The method further comprises driving an alternating current through the body via the first and the third electrode by means of a BIA circuitry comprised by the host device and sensing a voltage indicative of a body impedance of the body via the second and the fourth electrode by means of the BIA circuitry. Therein, the BIA circuitry is connected to the first and the second electrode via a first and a second line of the data cable, respectively.

Further implementations of the method are readily derived from the various implementations of the BIA system and vice versa. For further details regarding the method, it is referred to the explanations with respect to the BIA system.

The method may for example be used for recreational purposes, for purposes of information and/or further purposes that are not related to prophylaxis or curing of a medical condition or disease. For said purposes, it is further not necessary to compare the body impedance and/or the at least one biological parameter with reference values or medical reference values. The method may in particular not comprise steps that allow a detection of a medical symptom or a disease.

BRIEF DESCRIPTION OF THE DRAWINGS

In the following, the disclosure is explained in detail with the aid of exemplary implementations by reference to the drawings. Components that are functionally identical or have an identical effect may be denoted by identical references. Identical components and/or components with identical effects may be described only with respect to the figure where they occur first and their description is not necessarily repeated in subsequent figures.

In the drawings.

DETAILED DESCRIPTION

Figure 1:
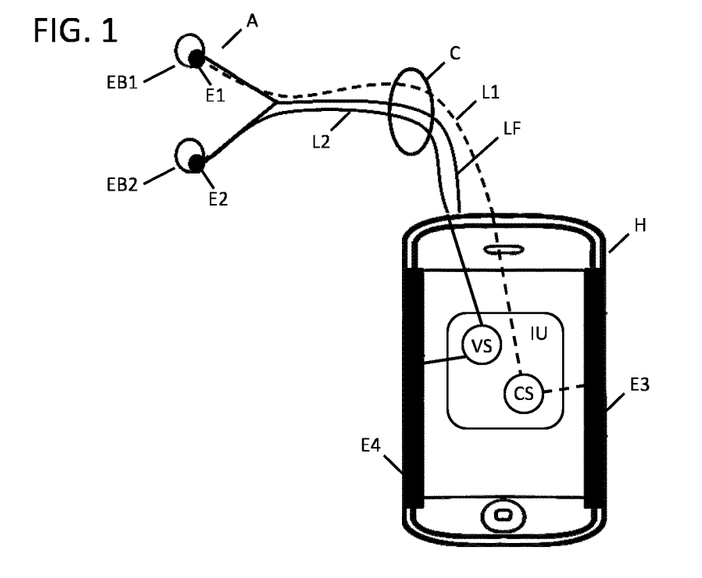
FIG. 1 shows an exemplary implementation of a BIA system according to the improved concept.

FIG. 1 shows an exemplary implementation of a bioelectrical impedance analysis, BIA, system according to the improved concept.

The BIA system comprises a portable electronic host device H, for example a smartphone, a tablet computer or a portable media player. The BIA system further comprises an accessory device A, for example an earphone device. The accessory device A has, for example, a data cable C, for example an audio cable. The accessory device A and the host device H may for example be connected by means of the data cable C.

The host device H comprises an interface unit IU, which may for example be implemented as an integrated circuit, IC, in particular a biometric IC. The interface unit IU comprises for example a current source CS and a voltage sensing unit VS. The host device H may, for example, further comprise an application processor (not shown) connected for example to the interface unit IU.

The accessory device A comprises, for example, a first component EB1, for example first speaker component, in particular a first earbud component, and a second component EB2, for example a second speaker component, in particular a second earbud component. The accessory device A comprises a first electrode E1 arranged on an outside of the first component EB1 and a second electrode E2 arranged on an outside of the second component EB2. The data cable C comprises a first line L1 connected to the first electrode E1 and a second line L2 connected to the second electrode E2. The data cable C may further comprise one or more further lines LF.

The host device H comprises a third electrode E3 and a fourth electrode E4. The third and the fourth electrode E3, E4 may, for example, be implemented as respective parts of a housing, in particular a case or a frame of the host device H. The third and the fourth electrodes E3, E4 are electrically isolated from each other. A first terminal of the current source CS is connected to the third electrode E3 and a first terminal of the voltage sensing unit VS is connected to the fourth electrode E4.

When the accessory device A is connected to the host device H via the data cable C, a second terminal of the current source CS is connected or switchably connected to the first line L1 and a second terminal of the voltage sensing unit VS is connected or switchably connected to the second line L2.

In operation, the first and the second electrode E1, E2 may, for example, contact first and second contact areas of a body of a user of the BIA system. The first and the second contact area may, for example, be located in, on or close to the ears of the user if the accessory device A is implemented as an earphone device. The third and the fourth electrode E3, E4 may, for example, be in contact with a third and a fourth contact area of the body of the user.

The interface unit IU may, for example, drive an alternating current through the body via the first and the third electrode E1, E3, in particular by means of the current source CS. The current may, for example, have a value, in particular an effective value, in the order of µA or tens µA. Consequently, an electromagnetic field may be established within the body of the user due to the driving of the current.

A voltage dropping across the second and the fourth electrode E2, E4 is, for example, sensed by the interface unit IU, in particular by the voltage sensing unit VS. The interface unit IU may then, for example, determine an amplitude value of the sensed voltage and a phase shift of the sensed voltage with respect to the alternating current.

The interface unit IU or, alternatively, the application processor may determine the body impedance of the body of the user depending on the sensed voltage, in particular depending on the amplitude value and the phase shift.

The application processor or, alternatively, the interface unit IU, may then for example determine at least one biological parameter of the body depending on the body impedance. The at least one biological parameter may for example include a body fat percentage or another parameter related to the body impedance.

Since the first and the second electrode E1, E2 may be located at increased spatial separations with respect to the third and the fourth electrode E3, E4, an accuracy of the determined body impedance may be increased due to increased respective conducting paths. Furthermore, since all calculations and computations are for example performed by the host device H, in particular by the interface unit IU and/or the application processor, there is no need for a processing unit such as a microprocessor or microcontroller unit in the accessory device A.

The data cable C is for example an audio cable. The first line L1 is for example a ground line, a microphone line or a speaker line of the data cable C. The same holds for the second line L2.

Figure 2:
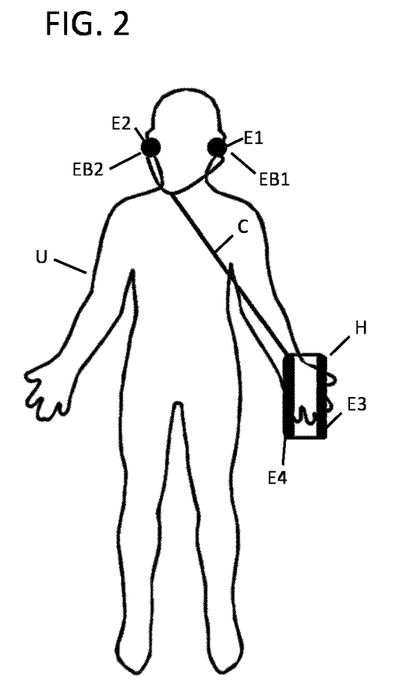
FIG. 2 shows an exemplary use case of a further exemplary implementation of a BIA system according to the improved concept.

FIG. 2 shows an exemplary use case of a further exemplary implementation of a BIA system according to the improved concept. The BIA system of FIG. 2 may, for example, be implemented as explained with respect to FIG. 1.

In the example of FIG. 2, the accessory device A is implemented as an earphone device with the first and the second speaker component EB1, EB2, for example as earbuds with the first and the second earbud component EB1, EB2.

FIG. 2 shows a user U wearing the accessory device A. For example, when wearing the accessory device A, the first and the second electrode E1, E2 contact the body of the user U, in particular at or in the user's ears.

Furthermore, the user may, for example, hold the host device H, for example implemented as a smartphone or a media player, in his hand. The third and the fourth electrode E3, E4 may, for example, be arranged on the outside of the host device H such that the user establishes a contact with respective third and fourth contact areas in the user's hand when holding the host device H, in particular always when holding the host device H in a designated manner. In some implementations, the third and the fourth electrode E3, E4 may be arranged such that the user U has to touch the third and the fourth electrode E3, E4, in particular intentionally, to establish the contact.

A BIA system according to the improved concept as shown in FIGS. 1 and 2 and used, for example, as in FIG. 2, may allow seamless measurement or determination of the body impedance and/or the biological parameter. In particular, the body impedance may for example be determined without a dedicated action of the user U being necessary except for wearing the accessory device A and holding and/or touching the host device H.

Figure 3:
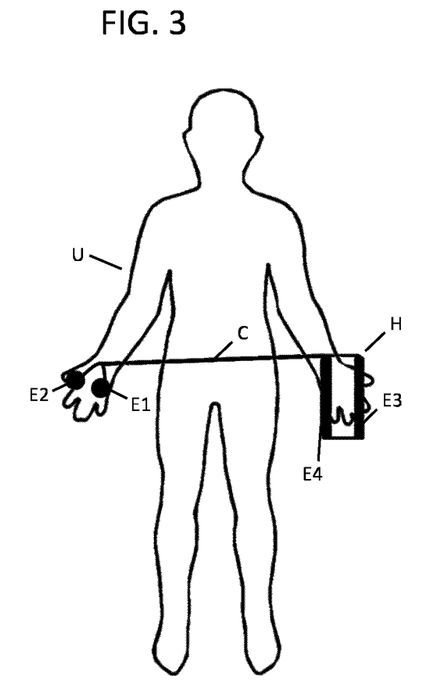
FIG. 3 shows a further exemplary use case of a further exemplary implementation of a BIA system according to the improved concept.

FIG. 3 shows a further exemplary use case of a further exemplary implementation of a BIA system according to the improved concept. The BIA system of FIG. 3 may, for example, correspond to the BIA system of FIG. 1 and/or FIG. 2.

In FIG. 3, the accessory device A may be implemented as an earphone device, for example as earbuds. However, in the use case of FIG. 3, the accessory device may also be implemented as another type of accessory device such as, for example, a dedicated accessory device for BIA having the first and the second electrode E1, E2 or a wristband, wristband, an ankle-band, a belt or a chest belt.

As in the use case of FIG. 2, the user U of FIG. 3 may establish a contact between the third and the fourth electrode E3, E4 and his body, in particular the third and the fourth contact area, by holding the host device H in his hand or by touching the third and the fourth electrode E3, E4. Furthermore, the user U may for example hold the accessory device A, in particular the first and the second electrode E1, E2, in his other hand and establish a contact to the first and the second contact area of his body in this way.

Figure 4:
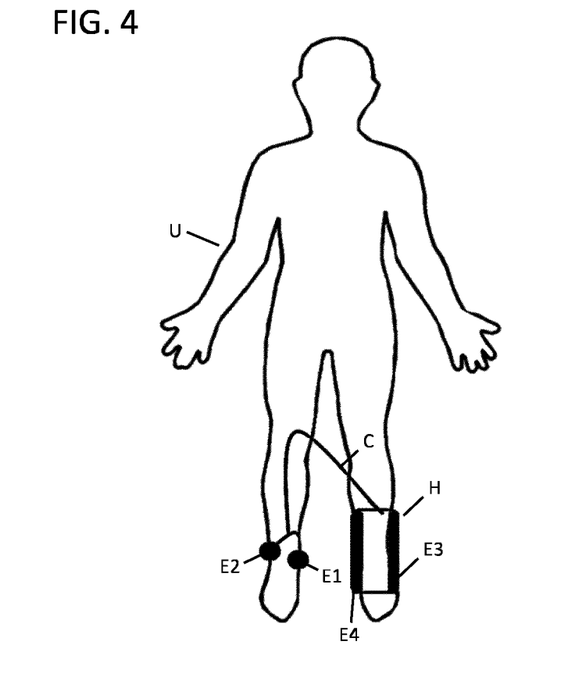
FIG. 4 shows a further exemplary use case of a further exemplary implementation of a BIA system according to the improved concept.

FIG. 4 shows a further exemplary use case of a further exemplary implementation of a BIA system according to the improved concept. The BIA system of FIG. 4 corresponds, for example, to the BIA system of FIG. 3.

In the use case of FIG. 4, the user U may, for example, establish a contact between the first and the second electrode E1, E2 and the first and the second contact area of his body by applying the first and the second electrode E1, E2 to a body part, for example a first leg of the user U. Analogously, the user U may for example establish a contact between the third electrode and the fourth electrode E3, E4 with the third and the fourth contact area of the body by applying the host device H, in particular the third and the fourth electrode E3, E4, to a further body part, for example a second leg of the user.

Figure 5:
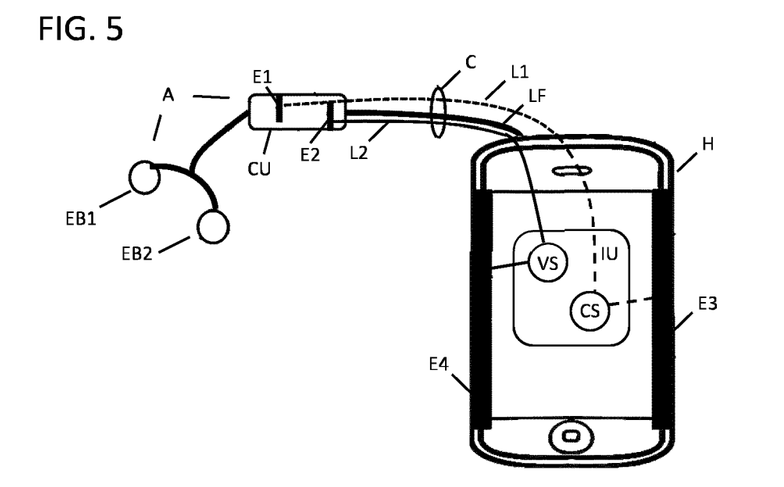
FIG. 5 shows a further exemplary implementation of a BIA system according to the improved concept.

FIG. 5 shows a further exemplary implementation of a BIA system according to the improved concept. The BIA system of FIG. 5 is based on the BIA system of FIG. 1.

The accessory device A is, for example, implemented as an earphone device. In contrast to the implementation of FIG. 1, the first and the second electrode E1, E2 are not arranged on the first and the second components EB1, EB2 of the accessory device A, respectively. Instead, the accessory device A comprises a control unit CU and the first and the second electrode E1, E2 are, for example, arranged on an outside of the control unit CU.

The control CU may, for example, be a volume control unit of the accessory device and/or a control unit for accepting, ending and/or rejecting a telephone call.

Figure 6:
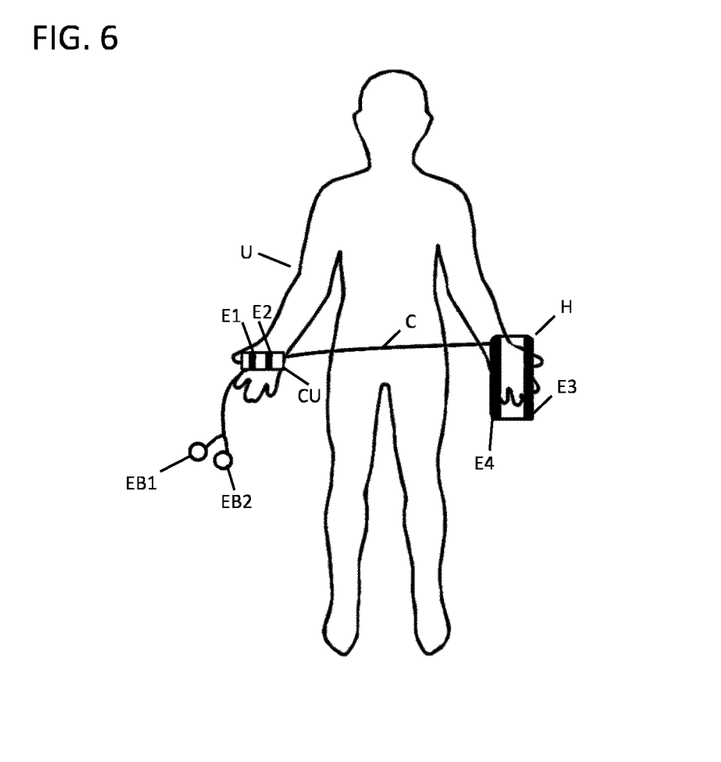
FIG. 6 shows a further exemplary use case of a further exemplary implementation of a BIA system according to the improved concept.

FIG. 6 shows a further use case of a further exemplary implementation of a BIA system according to the improved concept. The BIA system of FIG. 6 corresponds for example to the BIA system of FIG. 5.

The user U establishes for example a contact between the first and the second electrode E1, E2 and the first and the second contact area of his body by touching or holding the control unit CU. The contact between the third and the fourth electrode E3, E4 may for example be established as described with respect to FIGS. 2, 3 and 4.

The use cases of FIGS. 3, 4 and 6 may for example have the advantage of providing an improved accuracy of the determined body impedance. This may, for example, originate from the fact that the conducting path for the alternating current driven through the body via the first and the third electrodes E1, E3 may be particularly long in these cases.

Figure 7:
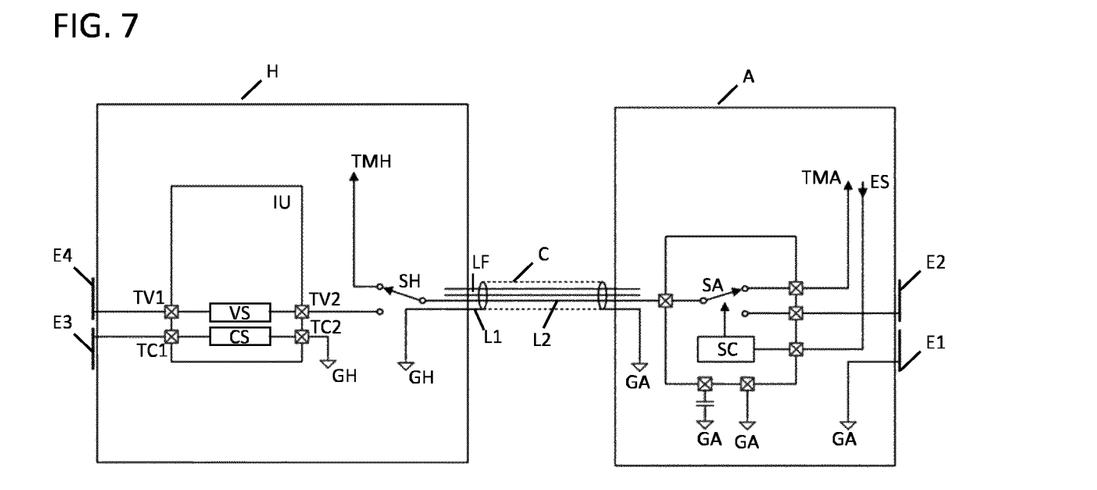
FIG. 7 shows a block diagram of a further exemplary implementation of a BIA system according to the improved concept.

FIG. 7 shows a block diagram of a further exemplary implementation of a BIA system according to the improved concept. The BIA system of FIG. 7 may, for example, correspond to one of the BIA systems of FIGS. 1 to 6. The accessory device A is for example, implemented as an earphone device.

In the implementation of FIG. 7, the first line L1 is for example a ground line of the data cable C. In particular, when the host device H and the accessory device A are connected to each other via the data cable C, the first line may for example connect a ground terminal of the accessory device GA to a ground terminal to host device GH. It is pointed out that the different ground terminals GH of the host device shown in FIG. 7 are for example electrically connected to each other and the various ground terminal so the accessory device GA shown in FIG. 7 are for example electrically connected to each other.

The first terminal TC1 of the current source is, for example, connected to the third electrode E3 and the second electrode TC2 of the current source CS is, for example, connected to the ground terminal GH of the host device H. Furthermore, the first electrode E1 is, for example, connected to the ground terminal GA of the accessory device A. Consequently, in operation, the BIA system may drive the alternating current by means of the current source CS via the ground line L1 of the data cable C and via the first and the third electrode E1, E3 through the body of the user.

The first terminal TV1 of the voltage sensing unit VS is, for example, connected to the fourth electrode E4 and the second electrode TV2 of the voltage sensing unit VS is, for example, connected to the second line L2 via a switch SH of the host device H. Furthermore, the second electrode E2 is, for example, connected via a switch SA of the accessory device A to the second line L2.

For example, the host device H may comprise a host microphone terminal TMH and the accessory device A may comprise an accessory microphone terminal TMA. The host microphone terminal TMH is connected to the second line L2, for example via the switch SH of the host device H and the accessory microphone terminal TMA is, for example, connected via the switch SA of the accessory device A to the second line L2.

Consequently, depending on a switch position of the switch SH, either the host microphone terminal TMH or the second terminal TV2 of the voltage sensing unit VS is connected to the second line. Analogously, depending on a switch position of the switch SA, either the accessory microphone terminal TMA or the second electrode E2 is connected to the second line L2. If the switches SH and SA connect the second terminal TV2 of the voltage sensing unit VS and the second electrode E2 to the second line L2, the interface unit IU may sense the voltage drop over the second and the fourth electrode E2, E4. On the other hand, if the microphone terminals TMH and TMA are connected to the second line via the switches SA and SH, respectively, the second line L2 may for example be used as a microphone line and microphone data may be exchanged between the microphone terminals TMH and TMA.

The accessory device A may, for example, further comprise a switch control SC configured to operate the switch SA of the accessory device A, for example depending on an enable signal ES. The enable signal ES may, for example, be generated depending on a user input, for example depending on a button press of the user on accessory device A. Alternatively or in addition, the enable signal ES may for example be generated by an audio communication interface (not shown), in particular by an accessory unit of the audio communication interface. In particular, the audio communication interface may control the switch SA to connect the accessory microphone terminal TMA to the second line L2 if microphone data shall be exchanged via the second line L2.

The switch SH of the host device H may, for example, be operated by the application processor of the host device H. For example, the application processor may control the switch SH of the host device H to connect the host microphone terminal TMH to the second line L2 if microphone data shall be exchanged via the second line L2.

Alternatively or in addition, the switch SH of the host device may be controlled by the audio communication interface, in particular by a host component of the audio communication interface. The host component and the accessory component of the audio communication interface may, for example, communicate to each other via the data cable C.

In this way it is possible that, for example, both switches SA, SH are controlled by the audio communication interface. For example, in case that microphone data shall be exchanged via the second line L2, the audio communication interface may control the switch SH of the host device H and may, for example, generate the enable signal ES to control the switch unit SC to control the switch SA of the accessory device A in order to connect both microphone terminals TMH and TMA to the second line L2.

By means of the improved concept, BIA may be performed by means of a portable electronic host device H together with an accessory device A. Improved accuracy is for example achieved by using a four-terminal measurement arrangement, where an effective conducting path between the respective electrodes is increased by implementing two electrodes E1, E2 in the accessory device A and two electrodes E3, E4 in the host device.

An implementation of four electrodes that are electrically isolated from each other may be complicated or hard to be implemented in a single portable electronic device such as the host device H. In this respect, the improved concept may provide an additional advantage.

The invention claimed is:

1. A bioelectrical impedance analysis, BIA, system comprising a portable electronic host device and an accessory device connectable to the host device via a data cable, the BIA system further comprising
 a first and a second electrode arranged on an outside of the accessory device for contacting a first and a second contact area of a body of a user, respectively;
 a third and a fourth electrode arranged on an outside of the host device for contacting a third and a fourth contact area of the body, respectively;
 a BIA circuitry comprised by the host device, the BIA circuitry being connectable to the first and the second electrode via a first and a second line, respectively, of the data cable, and connected to the third and the fourth electrode and configured to
  drive an alternating current through the body via the first and the third electrode;
  sense a voltage indicative of a body impedance of the body via the second and the fourth electrode; and
  determine the body impedance depending on the sensed voltage,
 wherein the portable electronic host device is a mobile phone, and
 wherein the accessory device is an earphone device.

2. The BIA system according to claim 1, wherein the BIA circuitry comprises an interface unit configured to
 drive the alternating current through the body and to sense the voltage indicative of the body impedance; and
 to determine an amplitude value of the sensed voltage and a phase shift of the sensed voltage with respect to the alternating current.

3. The BIA system according to claim 2, wherein
 the interface unit is configured to determine the body impedance depending on the amplitude value and the phase shift; or
 the BIA circuitry comprises a processing unit of the host device configured to determine the body impedance depending on the amplitude value and the phase shift.

4. The BIA system according to claim 3, wherein the BIA circuitry is configured to determine at least one biological parameter of the body depending on the body impedance.

5. The BIA system according to claim 1, wherein
 the BIA circuitry comprises a voltage sensing unit for sensing the voltage indicative of the body impedance; and
 the voltage sensing unit comprises a first terminal connected to the fourth electrode and a second terminal connectable to the accessory device via the second line.

6. The BIA system according to claim 1, wherein
 the BIA circuitry comprises a current source for driving the current through the body; and
 the current source comprises a first terminal connected to the third electrode and a second terminal connectable to the accessory device via the first line.

7. The BIA system according to claim 6, wherein
 the first electrode is connected to a ground terminal of the accessory device and the second terminal of the current source is connected to a ground terminal of the host device; and
 when the accessory device is connected to the host device via the data cable, the first line connects the ground terminals of the accessory device and the host device to each other.

8. The BIA system according to claim 1, wherein, when the accessory device is connected to the host device via the data cable,
 the second electrode is connected to the second line via a switch of the accessory device; and
 the second terminal of the voltage sensing unit is connected to the second line via a switch of the host device.

9. The BIA system according to claim 1, wherein
 the first and the second electrode are arranged on respective positions of the earphone device to contact the first and the second contact area when the user wears the earphone device.

10. The BIA system according to claim 1, wherein the data cable is implemented as an audio cable.

11. The BIA system according to claim 10, wherein the second line is useable as a microphone line or as a speaker line when the accessory device is connected to the host device via the data cable.

12. The BIA system according to claim 1, wherein the first line is useable as a ground line when the accessory device is connected to the host device via the data cable.

13. A method for determining a body impedance using a BIA system comprising a portable electronic host device and an accessory device connected to the host device via a data cable, the method comprising
 contacting a first and a second contact area of a body of a user with a first and a second electrode, respectively, arranged on an outside of the accessory device;
 contacting a third and a fourth contact area of the body with a third and a fourth electrode, respectively, arranged on an outside of the host device;
 driving an alternating current through the body via the first and the third electrode by means of a BIA circuitry comprised by the host device; and
 sensing a voltage indicative of a body impedance of the body via the second and the fourth electrode by means of the BIA circuitry;
 wherein BIA circuitry is connected to the first and the second electrode via a first and a second line, respectively, of the data cable,
 wherein the portable electronic host device is a mobile phone, and
 wherein the accessory device is an earphone device.

* * * * *